US006235296B1

(12) United States Patent
Daniel et al.

(10) Patent No.: US 6,235,296 B1
(45) Date of Patent: *May 22, 2001

(54) SKIN CLEANING AGENTS, A PROCESS FOR THEIR PRODUCTION AND THEIR USE

(75) Inventors: Günter Daniel, Krefeld; Volker Rosenberger, Kaarst; Beatrice Brücher, Krefeld, all of (DE)

(73) Assignee: Chemische Fabrik Stockhausen GmbH, Krefeld (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/199,486

(22) Filed: Nov. 25, 1998

Related U.S. Application Data

(63) Continuation of application No. 08/632,435, filed as application No. PCT/EP94/03448 on Oct. 20, 1994, now Pat. No. 5,891,449.

(30) Foreign Application Priority Data

Oct. 21, 1993 (DE) ................................. 43 35 933

(51) Int. Cl.$^7$ ..................................... A61K 7/50
(52) U.S. Cl. ........................... 424/401; 514/844; 514/846
(58) Field of Search ............................. 424/401; 514/844, 514/846

(56) References Cited

U.S. PATENT DOCUMENTS

| | | | |
|---|---|---|---|
| 3,560,614 | * 2/1971 | Embring et al. | 424/234 |
| 4,344,446 | 8/1982 | Ehrhardt . | |
| 4,707,293 | 11/1987 | Ferro . | |
| 5,476,661 | 12/1995 | Pillai et al. . | |
| 5,830,445 | * 11/1999 | Bouillon et al. | 424/69 |
| 5,891,614 | * 4/1999 | Daniel et al. | 424/401 |

FOREIGN PATENT DOCUMENTS

| | | |
|---|---|---|
| 693 350 | 7/1967 | (BE) . |
| 0 158 108 | 10/1985 | (EP) . |
| 0 513 832 | 11/1992 | (EP) . |
| 1 106 945 | 7/1967 | (GB) . |
| WO 89 03669 | 5/1989 | (WO) . |

OTHER PUBLICATIONS

Kirk–Othmer, Encyclopedia of Chemical Technology, Third Edition, vol. 5, p. 84, 1979.
Kirk–Othmer, Encyclopedia of Chemical Technology, Third Edition, vol. 6, p. 221, 1979.

* cited by examiner

*Primary Examiner*—Diana Dudash
*Assistant Examiner*—Shahnam Sharareh
(74) *Attorney, Agent, or Firm*—Oblon, Spivak, McClelland, Maier & Neustadt, P.C.

(57) ABSTRACT

The present invention relates to hydrous, liquid, paste- or cream-like skin cleaning agents for the removal of strongly adhering soil, comprising anionic and/or amphoteric and/or non-ionogenic surfactants as washing-active substances, thickeners, at least one abrasive, and, optionally, adjuvants for the regulation of consistency, appearance, odor, and stability, such as pigments, fragrances, stabilizers, and preservatives, which skin cleaning agents are characterized by the fact that they comprise di-n-butyl adipate and/or di-isopropyl adipate as the exclusive solvents. These agents are obtained by homogeneously mixing the components, optionally under heating of the mixture. If a $C_8$–$C_{16}$ fatty alcohol which acts as consistency regulator is added, heating of the component mixture may be omitted. Besides, the addition of the fatty alcohol increases the detergent action. The present invention further relates to the use of these skin cleaning agents, with the cleaning agent being distributed on the skin without water or with a small amount of water first, and the cleaning procedure being continued and finished under rinsing with water.

24 Claims, No Drawings

SKIN CLEANING AGENTS, A PROCESS FOR THEIR PRODUCTION AND THEIR USE

This application is a continuation of application Ser. No. 08/632,435 filed on May 31, 1996, now U.S. Pat. No. 5,891,449, which was filed as International Application No. PCT/EP94/03448, on Oct. 20, 1994.

The present invention relates to skin cleaning agents having an improved cleaning action and a gentle behavior to the skin. The present invention further relates to a process for their production and to the use of the agents as flowable hand cleaning agents and heavy-duty hand cleaning agents.

Hand cleaning agents, in particular for the removal of strongly adhering dirt, have already been used in the industrial sector for some time. Patent application No. WO 91/14420 describes cleaning agents which, in addition to anionic and/or non-ionogenic surfactants, comprise conventional abrasives, organic solvents in the form of carboxylic acid esters, in particular certain acetates, such as preferably n-butoxy-2-ethoxy-ethyl-acetate and fatty alkanolamides, fatty polyalkanolamides, the ethylene oxide and/or propylene oxide addition products thereof, as well as fatty acid monoglycerides as re-greasing agents. Another preferred, additionally used solvent in these hand cleansing agents is limonene, which is known to have a dermal incompatibility involving a sensitization risk. In order to produce the agents according to WO 91/14420 in an efficient manner, it is necessary to heat the mixture to temperatures above 50° C. after mixing the raw materials, requiring additional heating energy and involving longer production periods.

Furthermore, hand cleaning agents are known which comprise as solvent component natural oils, such as olive oil, jojoba oil, macadamia-nuts-oil, and grape-seed oil. These cleaning agents have limited detergent properties due to the interaction between the oil portions and the detergent portions and because of the low soil-removing capacity of the natural oil.

In cosmetics the use of special esters of the adipic acid is known. For instance, owing to its slightly greasing character, di-n-butyl adipate is used in day creams and liquid emulsions as well as in hair sprays and setting lotions as softening component or agent to achieve a superfatted state.

Patent No. GB 1,106,945 describes aqueous shampoo preparations for hair cleaning purposes; they comprise as solvents for fats alkyl esters of the dibasic carboxylic acids, phthalic acid or adipic acid. In hair cleaning and hair conditioning, particularly good results are obtained with dimethyl phthalate, however, there is no reference with respect to skin cleaning, in particular to the cleaning of skin heavily soiled by foreign substances.

EP 229 616 A2 describes bath additives comprising diisopropyl adipate as oil component which deposits on the skin.

EP 513 832 A1 describes pharmaceutical products comprising dibutyl adipate or a combination of dibutyl adipate and isopropyl myristate to improve or to control the skin penetration of a therapeutic agent.

Diisopropyl adipate is additionally used as lubricant in alcoholic lotions, as softener in hair aerosols and as fat factor in hair tonics and as solubilizer for perfumes.

PCT-application No. WO 92/09265 describes a solvent-containing hand cleaning paste containing as solvent DBE 2, dimethyl adipate, dimethyl glutarate and dimethyl succinate, in an amount up to 54 parts per 100 parts of cleaning agent, as well as isooctyl stearate as additionally required re-greasing agent and bleached kernel or shell flour as mild abrasive.

In EP No. 0166522 A2 a cosmetic preparation for the removal of nail varnish is described, which has also skin cleaning properties and comprises as solvent for the nail enamel esters of dicarboxylic acids, preferably diesters or esters of diols, preferably dioldiesters. The diethyl esters of dicarboxylic acids having up to 6 C-atoms are preferred as dicarboxylic acid esters, and the diacetates of diols having 2 to 6-C-atoms are preferred as diol esters. Additionally, the preparations contain lanolin or other re-greasing components and no abradant.

For this reason, the use of the known solvents in skin cleaning agents has made it necessary until today to compensate their intense effect on the skin by the action of re-greasing agents. However, the detergent action of the surfactants is slightly affected by the re-greasing components.

Accordingly, there was the object to provide skin cleaning agents and a process for their production, whose solvents have a comparable or improved cleaning action and thus an action which intensifies the cleaning effect, as well as an improved dermatologic compatibility. Additionally, there was the object to find a process for the manufacture of skin cleaning agents, in which heating of the raw material mixture may be omitted.

These objects have been achieved by skin cleaning agents which comprise as exclusive solvents di-n-butyl adipate and/or diisopropyl adipate and which, parallel to this, comprise as major components washing-active substances, components for the improvement of consistency, appearance, odor and storage stability, as well as at least one abrasive and water, and the production of which may be effected by using certain fatty alcohols in order to improve the cleaning action and the production conditions.

The subject matter of the present invention are hydrous, liquid, paste- or cream-like skin cleaning agents for the removal of strongly adhering dirt, which comprise anionic and/or amphoteric and/or non-ionogenic surfactants as washing-active substances, thickeners, at least one abrasive and, optionally, adjuvants for the regulation of consistency, appearance, odor, and stability, such as pigments, fragrances, stabilizers, and preservatives, and which are characterized in that they comprise di-n-butyl adipate and/or diisopropyl adipate as exclusive solvents. Known detergents are used as washing-active substances, in particular anionic and/or amphoteric and/or non-ionogenic surfactants, e.g., alkyl sulfates, alkyl sulfonates, alkyl ether sulfates, and fatty alcohol polyglycol sulfosuccinates, which are predominantly used in the form of their sodium salts, as well as the known non-ionogenic surfactants based on addition products of alkylene oxides to alkanols, alkanoic acids, which may also be capped at the end, and preferably alkyl polyglycosides.

Preferred surfactants include Na-lauryl ether sulfate, castor oil sulfonate, di-Na-lauryl polyglycol ether sulfosuccinate, cocoamidopropyl betaine, and alkyl polyglycosides having an alkyl residue of $C_8$–$C_{16}$, preferably $C_8$ to $C_{10}$ and an oligoglycoside residue having an oligomerization degree of 1.1–1.7, preferably 1.2–1.3.

The portion of the active detergents amounts to 5–40%-wt., preferably 10–30%-wt., relative to the skin cleaning agent according to the present invention.

The portion of the esters di-n-butyl adipate and/or diisopropyl adipate in the agents according to the present invention amounts to 1–25%-wt., preferably 5 to 20%-wt., and particularly preferred 10–20%-wt.

Abrasives to be used with preference are the bleached kernel/shell flours according to WO 92/09265, in particular bleached walnut shell flour or olive kernel flour. The portion of the abrasive in the agent according to the present invention amounts to 1–30%-wt., preferably 10–20%-wt.

The agents according to the present invention further comprise viscosity forming agents, such as organophilic and/or hydrophilic phyllosilicates, such as bentonites, polysaccharides, such as cellulose and guar flour, as well as modified polysaccharides, such as the cellulose ethers, carboxymethylcellulose, and hydroxyethyl-cellulose and xanthan gum, and inorganic electrolytes, such as NaCl or $MgSO_4$. They further comprise chromatophoric pigments, such as $TiO_2$, stabilizers, such as propylene carbonate, pH-regulators, fragrances, and preservatives. The water content of the skin cleaning agents amounts to 10–50%-wt., preferably 20–40%-wt.

Re-greasing components may be omitted in the production of the skin cleansing agents according to the present invention. Preferably, the skin cleaning agents are obtained as liquid or creamy agents or as flowable viscous pastes.

According to another preferred embodiment, the skin cleaning agents according to the present invention additionally comprise at least one fatty alcohol of the general formula R-OH wherein R represents an alkyl residue having $C_8$ to $C_{16}$, preferably $C_8$–$C_{12}$. The amount of the fatty alcohol in the agent amounts to 0.1–10.0%-wt., preferably 0.1–5.0%-wt.

The mentioned raw material components may usually also be employed by using combinations of one type of raw material, i.e., as mixtures of different surfactants, viscosity formers, abrasives, and stabilizers, etc.

The flowable skin cleansing agents are manufactured by means of known devices according to the batch or continuous method. Suitable devices are heatable vessels including an agitator, mixer and extruder, e.g., described in "Surfactants in Consumer Products", J. Falbe, Springer Verlag, 1987, page 399 ff.

The present invention further relates to a process for the production of the skin cleaning agents, in which the components are combined under stirring as usual, optionally using partial amounts of the raw materials, wherein the adipic ester solvents are preferably prepared first, and the pigment, viscosity forming agents/thickeners, and a partial amount of the surfactant are added then; this mixture is heated and preferably adjusted to a temperature of up to 70° C., preferably 40–60° C., whereupon the remaining raw material amounts, in particular surfactants amounts, the inorganic electrolyte, the pH-regulator and fragrance, the preservative, and the abrasive are added. The homogeneous mixture is then cooled and filled into conventional vessels, such as cans, pump vessels, such as dispensers, jars, and tubes.

According to a special production method according to the present invention, fatty alcohols are added as consistency regulators to produce the agents. Most surprisingly, it was found that the addition of the fatty alcohol allows the mixing the raw materials, e.g., in the succession as mentioned above, to form homogeneous products at room temperature, i.e., at 5 to 30° C., without having to heat the raw material mixture. The fact that the heating phase is omitted and the involved saving of energy and time offer advantages with respect to process technology.

Moreover, the addition of the fatty alcohol has a positive effect on the use of the skin cleansing agents since, for example, the detergent effect is increased.

The skin cleaning agents according to the present invention are particularly suitable for the removal of rough dirt strongly adhering to the skin, e.g., fats, oils and other lubricants, dyes, varnishes, tar, graphite, soot, coloring pigments, and similar substances occurring in industry and public utilities, in the craftsmen's trade, or in agriculture and in the household.

The use of the skin cleaning agents according to the present invention is preferably effected by first distributing the cleaning agent on the skin without water or with a small amount of water, continuing the cleaning with water and finishing by rinsing with water. The small amount of water results by wetting or moistening the soiled skin areas with water or aqueous liquids. For instance, in the case of dirty hands, this quantity may amount to about 1 to 3 ml of water per palm.

The agents according to the present invention can easily be distributed on the skin during washing. They have a good foaming power and—compared to conventional products—a better detergent action, with the dirt being easily removed from the skin with water. In addition to the good soil removing capacity, the agents according to the present invention have an improved dermatological compatibility.

Owing to the use of suitable raw materials the agents are biodegradable and, for this reason, are characterized by a good ecological compatibility.

The invention will be illustrated by the following examples:

| Formulation I | |
|---|---|
| Di-n-butyl adipate | 10.00% - wt. |
| Titanium dioxide | 1.00% - wt. |
| Organophilic bentonite | 2.10% - wt. |
| Carboxymethylcellulose | 1.20% - wt. |
| Sulfated castor oil (70%) | 10.53% - wt. |
| Propylene carbonate | 0.50% - wt. |
| Sodium fatty alcohol ether sulfate ($C_{12}$—$C_{15}$) 28% | 47.00% - wt. |
| Water | 0.19% - wt. |
| Di-sodium-lauryl polyglycol ether sulfosuccinate (32–35%) | 10.00% - wt. |
| Common salt | 2.00% - wt. |
| Citric acid | 0.20% - wt. |
| Fragrance | 0.20% - wt. |
| Preservative | 0.08% - wt. |
| Walnut shell flour, bleached | 15.00% - wt. |
| | 100.00% - wt. |

| Formulation II | |
|---|---|
| Di-isopropyl adipate | 10.00% - wt. |
| Titanium dioxide | 1.00% - wt. |
| Organophilic bentonite | 2.00% - wt. |
| Hydrophilic bentonite | 3.00% - wt. |
| Alkyl polyglycoside ($C_8$—$C_{10}$), 55% | 20.00% - wt. |
| Municipal water | 1.89% - wt. |
| Citric acid | 0.23% - wt. |
| Preservative | 0.08% - wt. |
| Boiled salt | 2.50% - wt. |
| Sodium fatty alcohol ether sulfate ($C_{12}$—$C_{15}$), 28% | 44.00% - wt. |
| Walnut shell flour, bleached | 15.00% - wt. |
| Fragrance | 0.30% - wt. |
| | 100.00% - wt. |

| Formulation III | |
|---|---|
| Solvent a to g*) | 10.00% - wt. |
| Titanium dioxide | 1.00% - wt. |
| Hydrophilic bentonite | 1.00% - wt. |
| Organophilic bentonite | 4.00% - wt. |
| Alkyl polyglycoside ($C_8$—$C_{10}$), 55% | 20.00% - wt. |
| Fatty alcohol ($C_8$—$C_{12}$) | 1.50% - wt. |
| Municipal water | 2.47% - wt. |
| Preservative | 0.08% - wt. |
| Fragrance | 0.30% - wt. |
| Citric acid | 0.15% - wt. |
| Common salt | 2.50% - wt. |
| Sodium fatty alcohol ether sulfate ($C_{12}$—$C_{15}$), 28% | 44.00% - wt. |
| Walnut shell flour, bleached | 13.00% - wt. |
| | 100.00% - wt. |

*)
IIIa: di-n-butyl adipate
IIIb: without solvent
IIIc: n-paraffin
IIId: grape-seed oil
IIIe: DBE 2
IIIf: di-isopropyl adipate
IIIg: di-n-butyl adipate, without fatty alcohol ($C_8$—$C_{12}$)

| Formulation IV | |
|---|---|
| Di-n-butyl adipate | 10.00% - wt. |
| Titanium dioxide | 1.00% - wt. |
| Hydrophilic bentonite | 1.00% - wt. |
| Organophilic bentonite | 3.00% - wt. |
| Alkyl polyglycoside ($C_8$—$C_{10}$), 55% | 20.00% - wt. |
| Fatty alcohol ($C_8$—$C_{12}$) | 4.00% - wt. |
| Municipal water | 0.97% - wt. |
| Preservative | 0.08% - wt. |
| Fragrance | 0.30% - wt. |
| Citric acid | 0.15% - wt. |
| Common salt | 2.50% - wt. |
| Sodium fatty alcohol ether sulfate ($C_{12}$—$C_{15}$), 28% | 44.00% - wt. |
| Walnut shell flour, bleached | 13.00% - wt. |
| | 100.00% - wt. |

| Formulation V | |
|---|---|
| Di-n-butyl adipate | 7.00% - wt. |
| Titanium dioxide | 1.00% - wt. |
| Hydrophilic bentonite | 1.00% - wt. |
| Organophilic bentonite | 2.50% - wt. |
| Alkyl polyglycoside ($C_8$—$C_{10}$), 55% | 20.00% - wt. |
| Fatty alcohol ($C_8$—$C_{12}$) | 8.00% - wt. |
| Municipal water | 0.47% - wt. |
| Preservative | 0.08% - wt. |
| Fragrance | 0.30% - wt. |
| Citric acid | 0.15% - wt. |
| Common salt | 0.50% - wt. |
| Sodium fatty alcohol ether sulfate ($C_{12}$—$C_{15}$), 28% | 44.00% - wt. |
| Walnut shell flour, bleached | 15.00% - wt. |
| | 100.00% - wt. |

The cleaning efficiency of the formulations was tested in the hand washing test according to the method described in DE 27 36 970 A1. It was found that the agents show a considerably improved cleaning action with respect to model soil mainly consisting of oil, wax, vaseline, graphite, lampblack, and iron oxide, and with respect to model varnish consisting of synthetic resin, fish oil, and a paint pigment.

The skin compatibility was tested in the Duhring chamber test [Frosch, P. J., Kligman, A. M.: The Duhring chamber and improved technique for epicutaneous testing of irritant and allergic reactions. Contact Derm. 5, 73–81 (1979); Frosch P. J., Kligman, A. M.: The soap chamber test, a new method of assessing the irritancy of soaps. J. Am. Acad. Derm. 1, 35–41 (1979)]. The results show that the dermal compatibility of the agents according to the present invention, as compared to commercially known products, is also improved.

Hand Washing Test

| Test person | Formulation I | IIIc | I | IIId | I | IIIe | II | IIIc | II | IIId | II | IIIa |
|---|---|---|---|---|---|---|---|---|---|---|---|---|
| 1 | 1.0 | 1.5 | 0.0 | 0.5 | 0.5 | 0.0 | 0.0 | 0.5 | 1.0 | 1.0 | 1.0 | 0.0 |
| 2 | 0.5 | 0.5 | 0.5 | 0.5 | 0.5 | 0.5 | 0.0 | 1.5 | 0.0 | 1.0 | 1.5 | 0.5 |
| 3 | 0.5 | 0.5 | 0.5 | 1.0 | 1.0 | 0.5 | 0.5 | 1.5 | 0.5 | 1.5 | 1.0 | 0.5 |
| 4 | 0.5 | 1.0 | 1.0 | 1.5 | 1.0 | 0.5 | 1.0 | 0.5 | 1.0 | 1.0 | 0.5 | 1.0 |
| 5 | 1.0 | 0.5 | 0.0 | 0.5 | 0.0 | 0.5 | 1.0 | 1.0 | 1.0 | 1.0 | 0.5 | 0.5 |
| 6 | 0.5 | 1.5 | 0.5 | 0.5 | 0.5 | 0.5 | 0.5 | 0.5 | 0.5 | 0.5 | 0.0 | 0.5 |
| Average | 0.6 | 0.9 | 0.4 | 0.8 | 0.6 | 0.4 | 0.5 | 0.9 | 0.7 | 1.0 | 0.8 | 0.5 |

| Test person | Formulation IIIa | IIIb | IIIa | IIIc | IIIa | IIId | IIIa | IIIe | IIIa | IIIf | IIIa | IIIg | IIIf | IIIe | IIIf | IIId |
|---|---|---|---|---|---|---|---|---|---|---|---|---|---|---|---|---|
| 1 | 0.5 | 0.5 | 0.5 | 0.0 | 0.0 | 1.5 | 0.5 | 0.5 | 1.0 | 2.0 | 0.0 | 1.5 | 0.5 | 0.5 | 0.5 | 1.0 |
| 2 | 0.0 | 1.0 | 0.5 | 0.0 | 0.0 | 0.5 | 0.0 | 0.5 | 1.0 | 1.0 | 0.5 | 1.0 | 0.0 | 0.5 | 0.5 | 0.5 |
| 3 | 0.0 | 2.0 | 0.5 | 1.0 | 0.0 | 1.0 | 1.5 | 1.0 | 0.5 | 0.5 | 0.5 | 1.0 | 1.5 | 1.0 | 1.0 | 1.5 |
| 4 | 0.5 | 0.5 | 0.5 | 0.5 | 1.0 | 0.5 | 0.5 | 1.0 | 0.0 | 1.0 | 0.5 | 1.0 | 1.0 | 0.5 | 0.5 | 0.5 |
| 5 | 0.0 | 1.0 | 0.5 | 2.5 | 0.0 | 0.5 | 1.5 | 1.0 | 0.5 | 0.5 | 0.0 | 1.0 | 2.0 | 1.5 | 1.5 | 2.5 |
| 6 | 0.1 | 0.5 | 0.5 | 2.0 | 1.0 | 1.0 | 2.0 | 2.5 | 2.0 | 1.5 | 1.5 | 1.5 | 0.5 | 0.0 | 1.0 | 1.0 |

-continued

| | | | | | | | | | | | | | | | | |
|---|---|---|---|---|---|---|---|---|---|---|---|---|---|---|---|---|
| Average | 0.3 | 0.9 | 0.5 | 1.0 | 0.3 | 0.8 | 1.0 | 1.1 | 0.8 | 1.1 | 0.5 | 1.2 | 0.9 | 0.7 | 0.8 | 1.2 |

IIIa: Formulation with di-n-butyl adipate
IIIb: Formulation without solvent
IIIc: Formulation with n-paraffin
IIId: Formulation with grape-seed oil
IIIe: Formulation with DBE2
IIIf: Formulation with di-isopropyl adipate
IIIg: Formulation with di-n-butyl adipate without fatty alcohol ($C_8$–$C_{12}$)
Amount of test product: 1.2 g
Amount of dirt: 0.5 g

RESULT

Both, formulation I with di-n-butyl adipate and formulation II with di-isopropyl adipate have a better detergent action than IIIc and IIId, but a slightly worse action than IIIe.

The washing tests clearly show the superiority of the formulation IIIa comprising di-n-butyl adipate and fatty alcohol ($C_8$–$C_{12}$), as compared with those without solvent (IIIb), with di-n-butyl adipate (IIIg), with n-paraffin (IIIc) and grape-seed oil (IIId).

In comparison with the formulations comprising DBE 2 (mixture of dimethyl adipate, dimethyl succinate, dimethyl glutarate), IIIe, and di-isopropyl adipate, IIIf, IIIa has a comparable or better detergent action.

Additionally, the formulation comprising diisopropyl adipate, IIIf, has a better cleaning effect than that comprising grape-seed oil, IIId, but a slightly worse one than the formulation with DBE 2, IIIe.

Duhring-Chamber-Test

| | Water | NaLS 0.5% | Formulation | | | | |
|---|---|---|---|---|---|---|---|
| | | | I | II | IV | V | IIIb |
| A-value | 25.1 | 4.3 | 16.1 | 14.4 | 14.8 | 15.3 | 14.2 |

| | Water | NaLS 0.5% | Formulation | | | | | |
|---|---|---|---|---|---|---|---|---|
| | | | IIIa | IIIc | IIId | IIIe | IIIf | IIIg |
| A-value | 25.1 | 4.3 | 15.2 | 5.0 | 17.1 | 8.2 | 14.7 | 14.5 |

IIIa: Formulation with di-n-butyl adipate
IIIb: Formulation without solvent
IIIc: Formulation with n-paraffin
IIId: Formulation with grape-seed oil
IIIe: Formulation with DBE2
IIIf: Formulation with di-isopropyl adipate
IIIg: Formulation with di-n-butyl adipate without fatty alcohol ($C_8$–$C_{12}$)
Amount of test product: appr. 200 mg
Duration of test: 3 weeks
Application intervals: 1st day 2 hours
2nd day 4 hours
3rd day 6 hours
4th day 6 hours
5th day about 5 hours
Number of test persons: 25

RESULT

The Duhring Chamber Test proves the good dermal compatibility of the formulations according to the present invention I, II, IV, IIIa, IIIf, and IIIg for this product class. In comparison, the formulations with n-paraffin (IIIc) and DBE 2 (IIIe) show a considerably worse skin compatibility.

What is claimed is:

1. A skin cleaning agent in hydrous, liquid, paste, or cream form comprising:
   1–25%-wt. of di-n-butyl adipate, di-isopropyl adipate, or a mixture thereof, as the only non-aqueous solvent component,
   a surfactant selected from the group consisting of anionic, amphoteric, nonionic surfactants and mixtures thereof, wherein the content of surfactant amounts to 5–40%-wt., relative to the skin cleaning agent,
   a thickener in an amount to affect the viscosity of the skin cleaning agent, and
   1–30%-wt. of at least one abrasive.

2. The skin cleaning agent of claim 1, further comprising, as a consistency regulator, at least one fatty alcohol of the formula R—OH wherein R is an alkyl residue having $C_8$–$C_{16}$.

3. The skin cleaning agent of claim 1, wherein the content of solvent amount to 5–20 wt. %, relative to the skin cleaning agent.

4. The skin cleaning agent of claim 2, wherein said at least one fatty alcohol is present in an amount of 0.1–10.0 wt. % relative to the skin cleaning agent.

5. The skin cleaning agent of claim 2, wherein said at least one fatty alcohol is present in an amount of 0.1–5.0 wt. %, relative to the skin cleaning agent.

6. The skin cleaning agent of claim 1, further comprising alkyl polyglycosides having an alkyl of $C_8$–$C_{16}$ and an oligoglycoside with an oligomerization degree of 1.1–1.7 as a non-ionic surfactant, sodium fatty alcohol ether sulfate as an anionic surfactant and bleached walnut shell flour as an abrasive.

7. The skin cleaning agent of claim 1, wherein the content of surfactant is 10–20 wt. %.

8. The skin cleaning agent of claim 1, wherein said at least one abrasive is present in an amount of 10–20 wt. %.

9. The skin cleaning agent of claim 1, further comprising water in an amount of 10–50 wt. %.

10. The skin cleaning agent of claim 1, further comprising water in an amount of 20–40 wt. %.

11. A process for the production of the skin cleaning agent of claim 1, comprising:
    preparing the solvent first, adding the pigment, thickener and a partial amount of the surfactant, heating the mixture thus obtained to a temperature of up to 70° C., adding the remaining amounts of components, followed by homogenization and final cooling.

12. The process of claim 11, wherein the skin cleaning agent further comprises, as a consistency regulator, 0.1–5.0% of a fatty alcohol, and the mixing of the components and the homogenization is effected without heating.

13. A method of cleansing the skin, comprising:
distributing the skin cleaning agent of claim 1 on the skin, and rinsing the skin with water.

14. The skin cleaning agent of claim 1, further comprising one or more pigments, fragrances, stabilizers and preservatives.

15. The skin cleaning agent of claim 2, wherein said R is $C_8$–$C_2$ alkyl.

16. The method of claim 13, wherein said skin cleaning agent comprises alkyl polyglycosides having an alkyl of $C_8$–$C_{10}$ and an oligoglycoside with an oligomerization degree of 1.1–1.7 as a non-ionic surfactant, sodium fatty alcohol ether sulfate as an anionic surfactant and bleached walnut shell flour as an abrasive.

17. The method of claim 16, wherein said oligoglycoside has an oligomerization degree of 1.2–1.3.

18. The process of claim 11, wherein said mixture is heated to a temperature of 40–60° C.

19. The process of claim 11, wherein said components comprise surfactant, inorganic electrolyte, pH-regulator, fragrance, preservative and abrasive.

20. The skin cleaning agent of claim 1, wherein said abrasive comprises bleached walnut shell flour.

21. The skin cleaning agent of claim 1, wherein said non-ionic surfactant is an alkyl polyglycoside having an alkyl of $C_8$–$C_{16}$ and an oligoglycoside with an oligomerization degree of 1.1–1.7, and wherein said anionic surfactant is sodium fatty alcohol ether sulfate.

22. The skin cleaning agent of claim 1, wherein said anionic, amphoteric and nonionic surfactants are selected from the group consisting of alkyl sulfate, sodium salt of alkyl sulfate, alkyl sulfonate, sodium salt of alkyl sulfonate, alkyl ether sulfate, sodium salt of alkyl ether sulfate, fatty alcohol polyglycol sulfosuccinate, sodium salt of fatty alcohol polyglycol sulfosuccinate, addition product of alkylene oxide to alkanol, alkanoic acid, alkanoic acid capped at the end, sodium lauryl ether sulfate, castor oil sulfonate, sodium lauryl ether sulfate, disodium lauryl polyglycol ether sulfosuccinate, cocoamidopropyl betaine, alkyl polyglycoside having an alkyl residue of $C_8$–$C_{16}$ and an oligoglycoside residue having an oligomerization degree of 1.1–1.7, alkyl polyglycoside having an alkyl residue of $C_8$–$C_{10}$ and an oligoglycoside residue having an oligomerization degree of 1.2–1.3.

23. The skin cleaning agent of claim 1, comprising at least one amphoteric surfactant.

24. The skin cleaning agent of claim 1, comprising at least one amphoteric surfactant in combination with at least one selected from the group consisting of anionic and nonionic surfactant.

* * * * *